US010934562B2

(12) United States Patent
Tracy et al.

(10) Patent No.: US 10,934,562 B2
(45) Date of Patent: *Mar. 2, 2021

(54) INTEGRATED MIXOTROPHIC FERMENTATION METHOD

(71) Applicant: White Dog Labs, Inc., New Castle, DE (US)

(72) Inventors: Bryan Patrick Tracy, Wilmington, DE (US); Sasson R. Somekh, Los Altos Hills, CA (US); John Randall Phillips, Middletown, DE (US); Aharon M. Eyal, Jerusalem (IL)

(73) Assignee: White Dog Labs, Inc., New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,976

(22) PCT Filed: May 23, 2017

(86) PCT No.: PCT/US2017/033979
§ 371 (c)(1),
(2) Date: Nov. 19, 2018

(87) PCT Pub. No.: WO2017/205363
PCT Pub. Date: Nov. 30, 2017

(65) Prior Publication Data
US 2019/0144892 A1 May 16, 2019

Related U.S. Application Data

(60) Provisional application No. 62/340,202, filed on May 23, 2016.

(51) Int. Cl.
*C12P 7/06* (2006.01)
*C12P 7/54* (2006.01)
(Continued)

(52) U.S. Cl.
CPC ............. *C12P 7/065* (2013.01); *A61K 35/74* (2013.01); *C12P 7/04* (2013.01); *C12P 7/06* (2013.01);
(Continued)

(58) Field of Classification Search
None
See application file for complete search history.

(56) References Cited

U.S. PATENT DOCUMENTS 5,173,429 A   12/1992   Gaddy et al.
9,938,542 B2   4/2018   Tracy et al.
(Continued)

FOREIGN PATENT DOCUMENTS

DE   102011054298   4/2013

OTHER PUBLICATIONS

Fast et al., Curr. Opin. Biotechnol. 33: 60-72 (2015).*
(Continued)

*Primary Examiner* — Erin M. Bowers
(74) *Attorney, Agent, or Firm* — Eva Taksel (57) ABSTRACT

Integrated mixotrophic fermentation method comprising (i) an isolated naturally acetogenic organism; (ii) a first feedstock comprising a carbon source for use in a fermentation medium; (iii) a second feedstock comprising elemental hydrogen for use in the fermentation medium; wherein the second feedstock comprises performing electrolysis; and (iv) culturing the organism in the fermentation medium, whereby both feedstocks are metabolized and a fermentation broth is formed, which broth comprises at least one bioproduct.

20 Claims, 2 Drawing Sheets

Specification includes a Sequence Listing.

(51) Int. Cl.

| | |
|---|---|
| C12P 7/04 | (2006.01) |
| C12P 7/16 | (2006.01) |
| C12P 7/24 | (2006.01) |
| C12P 7/52 | (2006.01) |
| A61K 35/74 | (2015.01) |
| C12P 7/18 | (2006.01) |
| C12P 7/28 | (2006.01) |
| C12P 7/62 | (2006.01) |
| A61K 35/00 | (2006.01) |

(52) U.S. Cl.
CPC .................................. *C12P 7/16* (2013.01); *C12P 7/18* (2013.01); *C12P 7/24* (2013.01); *C12P 7/28* (2013.01); *C12P 7/52* (2013.01); *C12P 7/54* (2013.01); *C12P 7/62* (2013.01); *A61K 35/00* (2013.01); *Y02E 50/10* (2013.01)

(56) References Cited

U.S. PATENT DOCUMENTS

| | | | |
|---|---|---|---|
| 2010/0120104 A1* | 5/2010 | Reed | C12N 1/20 435/140 |
| 2010/0273229 A1 | 10/2010 | Verser et al. | |
| 2012/0064587 A1 | 3/2012 | Papoutsakis et al. | |
| 2014/0342426 A1 | 11/2014 | Angelidaki et al. | |
| 2015/0037832 A1* | 2/2015 | Scholz | C12P 7/20 435/29 |
| 2015/0259639 A1 | 9/2015 | Silverman et al. | |

OTHER PUBLICATIONS

Reith et al., Proceedings of the 12th European Conference on Biomass for Energy, Industry, and Climate Protection, pp. 1-6 (2002).*

Reith et al., "Co-Production of Bio-Ethanol, Electricity and Heat from Biomass Residues", *Proceedings of the 12th European Conference on Biomass for Energy, Industry and Climate Protection*, retrieved from the internet: <4solarenergy2.nl/downloads/0492bioethanol--ecn-rx02030.pdf>, pp. 1-6 (2002).

Fast et al., "Acetogenic Mixotrophy: Novel Options for Yield Improvement in Biofuels and Biochemicals Productions", *Current Opinion in Biotechnology*, vol. 33, pp. 60-72, published online Dec. 10, 2014.

Bertsch et al., "CO Metabolism in the Acetogen *Acetobacterium woodii*", *Applied and Environmental Microbiology*, vol. 81, No. 17, pp. 5949-5956 (2015).

Freude et al., "Carbon Isotope Fractionation during Catabolism and Anabolism in Acetogenic Bacteria Growing on Different Substrates", *Applied and Environmental Microbiology*, vol. 82, No. 9, pp. 2728-2737 (2016).

Ueki et al., "Converting Carbon Dioxide to Butyrate with an Engineered Strain of *Clostridium ljungdahlii*", *mBio*, vol. 5, No. 5, pp. 1-10 (2014).

Dwidar et al., "The Future of Butyric Acid in Industry", *The Scientific World Journal*, vol. 2012, No. 13, pp. 1-9 (2012).

Jones et al., "$CO_2$ Fixation by Anaerobic Non-Photosynthetic Mixotrophy for Improved Carbon Conversion", *Nature Communications*, vol. 7, Iss. 12800, pp. 1-9 (2016).

International Search Report for PCT/US2017/033979, dated Aug. 16, 2017.

Written Opinion of the ISA for PCT/US2017/033979, dated Aug. 16, 2017.

U.S. Appl. No. 62/340,202, filed May 23, 2016.

* cited by examiner

SEQUENCE LISTING

<160> NUMBER OF SEQ ID NOS: 1

<210> SEQ ID NO 1
<211> LENGTH: 1056
<212> TYPE: DNA
<213> ORGANISM: C. ljungdahlii

<400> SEQUENCE: 1

```
atgaaaggtt ttgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aataggaaa atatgatttt aggccatgaa      180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagtttccca attttaaaga tggtgtatttt    360 gcagattact ttcatgtaaa cgatgcagat atgaatcttg ccatactccc agatgaaata     420
cctttagaaa gtgcagttat gatgacagac atgatgacta ctggttttca tggagcagaa     480
cttgcagaca taaaaatggg ctccagcgtt gtagtaattg gtataggagc tgttggatta     540
atgggaatag ccggttccaa acttcgagga gcaggcagaa ttatcggtgt tggaagcaga     600
cctgtttgtg ttgaaacagc taaattttat ggagcaactg atattgtaaa ttataaaaat     660
ggtgatatag ttgaacaaat catggactta actcatggta aagtgtaga ccgtgtaatc      720 atggcaggcg gtggtgctga aacactagca caagcagtaa ctatggttaa acctggcggc     780
gtaatttcta acatcaacta ccatggaagc ggtgatactt taccaatacc tcgtgttcaa     840
tggggctgcg gcatggctca caaaactata agaggaggat tatgccccgg cggacgtctt     900
agaatggaaa tgctaagaga tcttgttcta tataaacgtg ttgatttgag taaacttgtt     960
actcatgtat ttgatggtgc agaaaatatt gaaaaggccc ttttgcttat gaaaaataag    1020
ccaaaagatt taattaaatc agtagttaca ttctaa                              1056
```

INTEGRATED MIXOTROPHIC FERMENTATION METHOD

CROSS REFERENCE TO RELATED APPLICATIONS

The instant application claims priority to U.S. Provisional Application No. 62/340,202, filed May 23, 2016, the disclosure of which is incorporated by reference herein in its entirety.

FIELD OF THE INVENTION

The field of art to which this invention generally pertains is mixotrophic fermentation, feedstocks, and integrated energy conversion methods.

BACKGROUND OF THE INVENTION

The production costs for biofuels and certain other bioproducts via microbial fermentation is currently high, particularly compared to oil-derived fuels. Feedstock and feedstock pre-treatment costs for use in such methods can form 50-60% or more of total operating costs. Generally these costs relate to the carbohydrates used as the carbon source in the production of the biofuels. Because these costs are so high, they are one of the primary factors affecting the economic viability of cellulosic and other next generation biofuel manufacturing processes. There is therefore a strong need for lowering these costs and for producing desired products at high yield and high titers. One way to mitigate high feedstock costs is by maximizing feedstock conversion to the product of interest.

However, conventional methods for maximizing feedstock conversion are fraught with difficulties. For example, attempts to ferment gaseous substrates with autotrophic organisms have been hindered by difficulties in reaching suitable concentrations of the substrate and by low titers, which increase isolation-related operating costs. Autotrophic fermentation has also been limited in the range of economically attainable products.

From a metabolic perspective, acetyl-CoA is a central building block and a link between glycolysis and fermentative alcohol production. Consequently acetyl-CoA serves as a focal point for biofuel production in microbial organisms. However, the ability to achieve metabolically efficient production of acetyl-CoA (and high mass yields) has historically been impeded by $CO_2$ loss during decarboxylation reactions involved in classical Embden-Meyerhof-Parnas (EMP) glycolysis. For example, one molecule of glucose (where glucose is the carbon source) under heterotrophic growth conditions may be used to generate two molecules of acetyl-CoA and excess ATP (adenosine triphosphate), but this occurs at the "expense" of two $CO_2$ molecules, which are lost in the conversion of pyruvate to acetyl-CoA. In contrast, two molecules of $CO_2$ (where gaseous $CO_2$ is the carbon source) under autotrophic growth conditions may generate one molecule of acetyl-CoA, but this scheme results in a net ATP formation of less than 1, and acetate production (from acetyl-CoA) is required to generate more ATP.

Accordingly, there is a need for fermentation methods and engineered metabolic pathways that minimize—or ideally eliminate—$CO_2$ losses and result in complete conversion of a carbohydrate source into acetyl-CoA without having to sacrifice the acetyl-CoA produced for further generation of ATP.

SUMMARY OF THE INVENTION

Provided is an integrated mixotrophic fermentation method comprising (i) providing an isolated naturally acetogenic organism; (ii) providing a first feedstock comprising a carbon source for use in a fermentation medium; (iii) providing a second feedstock comprising elemental hydrogen gas for use in the fermentation medium; wherein the providing a second feedstock comprises performing electrolysis; and (iv) culturing the organism in the fermentation medium, whereby both feedstocks are metabolized and a fermentation broth is formed, which broth comprises at least one bioproduct.

According to an embodiment, the organism is not naturally occurring.

According to an embodiment, the providing a second feedstock further comprises at least one operation selected from (a) hydrocarbon reforming, (b) biomass-derived liquid reforming; (c) partial oxidation; (d) biomass gasification, (e) coal gasification, and (f) water-gas shift reaction.

According to an embodiment, the providing a second feedstock further comprises at least one of partial oxidation and biomass gasification.

According to an embodiment, the electrolysis generates oxygen and at least a fraction of the generated oxygen is used for providing a second feedstock via at least one of partial oxidation and biomass gasification.

According to an embodiment, the electrolysis is performed at off-peak hours.

According to an embodiment, the method further comprises (a) processing a lignocellulosic biomass to produce separated carbohydrate solution and separated lignin and (b) using the separated carbohydrate solution in the providing a first feedstock.

According to an embodiment, the method further comprises burning or partially oxidizing at least a fraction of the separated lignin to generate electricity and using at least a fraction of the electricity in the electrolysis.

According to an embodiment, the method further comprises providing electricity to the grid at peak hours. For example, the method may comprise transferring energy to a convention power grid to provide, e.g., electricity to consumers or to generate additional hydrogen for use in mixotrophic fermentation.

According to an embodiment, the method further comprises providing electricity to the grid on demand.

According to an embodiment, the method further comprises operating the electrolysis at off-peak hours.

According to an embodiment, the method further comprises operating the electrolysis with interruptible power from the grid.

According to an embodiment, the method further comprises gasifying at least a fraction of the separated lignin for providing the second feedstock.

According to an embodiment, the provided first feedstock, the provided second feedstock or both comprise supplemented $CO_2$.

According to an embodiment, the carbon yield based on the total amount of carbon in produced bioproducts divided by the total amount of carbon metabolized from the carbon source is at least 67%.

According to an embodiment, the bioproduct comprises ethanol and the carbon yield based on the total amount of carbon in produced ethanol divided by the total amount of carbon metabolized from the carbon source is at least 67%.

According to an embodiment, the first feedstock comprises a carbohydrate selected from glucose and sucrose, and the organism metabolizes $CO_2$ produced on metabolizing the carbohydrate.

According to an embodiment, the first feedstock comprises glycerol, $CO_2$ is produced on metabolizing the glycerol, and the organism metabolizes the $CO_2$.

According to an embodiment, the carbon source is metabolized by the native form of the organism at a rate of less than 0.01 g/hr/g cell mass.

According to an embodiment, the method yields a greater amount of the at least one bioproduct than the combined amounts of the at least one bioproduct produced by heterotrophic and autotrophic fermentation with the same organism under the same conditions.

According to an embodiment, the method yields a greater amount of the at least one bioproduct than the amount of the at least one bioproduct produced by heterotrophic fermentation with the same organism under the same conditions.

According to an embodiment, the method comprises production of a first bioproduct and acetic acid as a second bioproduct, and the amount of acetic acid produced per biomass unit weight is less than about 50% of that produced in autotrophic fermentation with the same organism under the same conditions.

According to an embodiment, the $^{13}C/^{12}C$ isotope ratio of the carbon present in the bioproduct is less than that of atmospheric $CO_2$.

According to an embodiment, the organism is a bacterium. According to an embodiment, the bacterium belongs to the Clostridia family. According to an embodiment, the clostridia is of *Clostridium* genus.

According to an embodiment, the organism is selected from *Clostridium ljungdahlii*, *Clostridium autoethanogenum*, *Clostridium ragsdalei*, *Clostridium aceticum*, *Clostridium carboxidivorans*, *Clostridium drakei*, *Clostridium formicoaceticum*, *Clostridium scatologenes*, *Clostridium glycolicum*, *Clostridium magnum*, *Clostridium mayombei*, and *Clostridium methoxybenzovorans*.

According to an embodiment, the organism is a genetically modified Clostridia.

According to an embodiment, the first feedstock and the second feedstock are present in the fermentation medium at the same time.

According to an embodiment, the bioproduct is non-naturally occurring.

According to an embodiment, the bioproduct is selected from the group consisting of even numbered primary alcohols, odd numbered secondary alcohols, organic acids of less than 7 carbons, C3 compounds, C4 compounds, and mixtures thereof.

According to an embodiment, the bioproduct comprises ethanol.

According to an embodiment, the bioproduct comprises acetone.

According to an embodiment, the bioproduct comprises isopropanol.

According to an embodiment, the bioproduct comprises butanol.

According to an embodiment, the bioproduct comprises butyric acid.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Provided is an integrated mixotrophic fermentation method comprising (i) providing an isolated naturally acetogenic organism; (ii) providing a fermentation medium first feedstock comprising a carbon source; (iii) providing a fermentation medium second feedstock comprising elemental hydrogen gas; wherein the providing a second feedstock comprises electrolysis; (iv) culturing the organism in the fermentation medium, whereby both feedstocks are metabolized and a fermentation broth is formed, which broth comprises at least one bioproduct.

The method comprises providing an isolated, naturally occurring or non-naturally occurring organism capable of metabolizing $CO_2$. According to an embodiment, the organism is non-naturally occurring. The organism may be autotrophic. In an embodiment, the organism may be capable of assimilating CO, $CO_2$, methanol, etc., for growth. The organism may also be capable of utilizing glycolysis for growth. Any organism capable of metabolizing $CO_2$ is suitable. According to an embodiment, the organism is acetogenic. In an embodiment, the organism is naturally acetogenic. An organism is "naturally acetogenic" if the wild-type (or native) organism is capable of metabolizing $CO_2$ into acetate using the Wood-Ljungdahl pathway (WLP) (or reductive acetyl-CoA pathway). A naturally acetogenic organism may be a wild-type organism or genetically modified.

Figure 1:
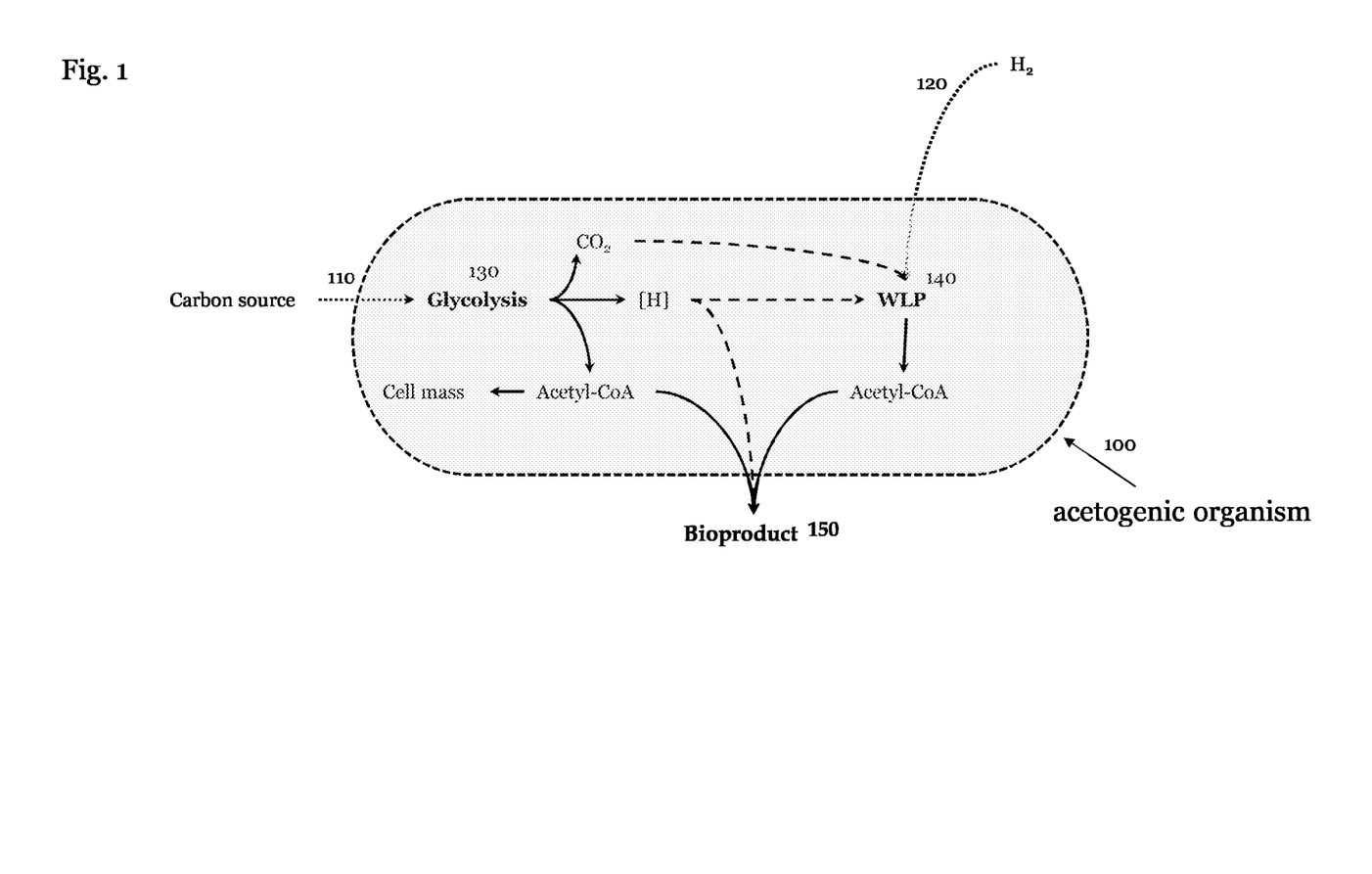
FIG. 1 shows an embodiment of integrated mixotrophy fermentation method of one possible acetogenic organism.

FIG. 1 shows an embodiment of integrated mixotrophy fermentation method of one possible isolated naturally acetogenic organism (100). Carbon source (110) is provided to the fermentation medium and is metabolized by the isolated naturally acetogenic organism (100). Second feedstock to the fermentation medium is $H_2$ gas (120). According to some embodiment, the acetogenic organism uses Glycolysis (130) and the Wood-Ljungdahl pathway (WLP) (140) during metabolism to produce a bioproduct, which may be a metabolite (150).

According to an embodiment, the organism is Clostridia. According to an embodiment, the clostridia is of *Clostridium* genus. According to an embodiment, the organism is acetogenic Clostridia. According to an embodiment, the organism is a genetically modified Clostridia.

According to an embodiment, the organism may be selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Clostridium carboxidivorans, Alkalibaculum bacchi, Clostridium drakei, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxrobacter pfennigii,* and *Thermoanaerobacter kivui.*

The organism may be genetically modified. For example, the organism may be genetically modified to reduce or eliminate expression of a primary alcohol dehydrogenase, a secondary alcohol dehydrogenase, a bifunctional aldehyde/alcohol dehydrogenase, or an aldehyde oxidoreductase. In an embodiment, the organism may be genetically modified to have a primary alcohol dehydrogenase gene, a secondary alcohol dehydrogenase gene, a bifunctional aldehyde/alcohol dehydrogenase, or an aldehyde oxidoreductase deleted from its genome. While a genomic deletion is a preferred embodiment, any genomic mutation resulting in inactivation of the enzyme would be sufficient, including but not limited to partial gene deletion, nonsense mutation, transcriptional promoter deletion, etc. In another embodiment, the transcriptional expression of this gene can be reduced by using antisense RNA.

As used herein, a "primary alcohol dehydrogenase" is an enzyme that catalyzes the reduction of an aldehyde to a primary alcohol, for example, the reduction of acetaldehyde to ethanol. As used herein, a "secondary alcohol dehydrogenase" is an enzyme that catalyzes the reduction of a ketone to a secondary alcohol, for example, the reduction of acetone into 2-propanol (a.k.a. isopropanol). As used herein, a "bifunctional aldehyde/alcohol dehydrogenase" is an enzyme that catalyzes both the acetylating and reduction reactions to take, for example, acetyl-CoA to acetyladehde and then ethanol. As used herein, an "aldehyde oxidoreductase" is an enzyme that catalyzes the reduction of a carboxylate to an aldehyde, for example, the reduction of acetate to acetaldehyde. Exemplary examples in *C. ljungdahlii* DSM 13528 are genes CLJU_c11880 and CLJU_c39670 for a primary alcohol dehydrogenase, CLJU_c24860 and CLJU_c23220 for a secondary alcohol dehydrogenase, CLJU_c6510 and CLJU_c16520 for a bifunctional aldehyde/alcohol dehydrogenase, and CLJU_c200110 and CLJI_c20210 for an aldehyde oxidoreductase.

According to an embodiment, the providing a second feedstock further comprises at least one of (a) hydrocarbon reforming, (b) biomass-derived liquid reforming; (c) partial oxidation; (d) biomass gasification, (e) coal gasification, and (f) water-gas shift reaction.

According to an embodiment, the providing a second feedstock comprises water-gas shift reaction. As used herein, the term water-gas shift reaction refers to the reaction between CO and water, wherein $CO_2$ and hydrogen are formed. According to an embodiment, water is introduced to the reaction as steam. According to an embodiment, a catalysts is used.

$$CO+H_2O \rightarrow CO_2+H_2$$

According to an embodiment, carbon dioxide and other impurities are removed from the gas stream, e.g. via pressure-swing adsorption, leaving essentially pure hydrogen.

According to an embodiment, the providing a second feedstock comprises hydrocarbon reforming, wherein a hydrocarbon reacts with water. According to an embodiment, the hydrocarbon comprises methane. Any source of methane is suitable. According to an embodiment, methane is provided as natural gas. According to another embodiment, the method further comprises anaerobic fermentation, wherein methane is formed. According to an embodiment, high-temperature steam (e.g. at 700° C.) reacts with methane under pressure, optionally in the presence of a catalyst, whereby hydrogen and carbon monoxide are formed. According to an embodiment, the method further comprises reacting at least a fraction of the formed carbon monoxide with steam according to the water-gas shift reaction.

$$CH_4+H_2O \rightarrow CO+3H_2$$

$$CO+H_2O \rightarrow CO_2+H_2$$

According to an embodiment, the providing a second feedstock comprises biomass-derived liquid reforming. According to an embodiment, the method comprises converting biomass into a product (e.g. ethanol, bio-oils) and reforming the product to produce hydrogen and CO. According to an embodiment, the method further comprises reacting at least a fraction of the formed carbon monoxide with steam according to the water-gas shift reaction.

$$C_2H_5OH+H_2O \rightarrow 2CO+4H_2$$

$$CO+H_2O \rightarrow CO_2+H_2$$

According to an embodiment, the providing a second feedstock comprises partial oxidation. According to an embodiment, a hydrocarbon, e.g. methane reacts with a limited amount of oxygen to generate hydrogen and carbon monoxide. According to an embodiment, the method further comprises reacting at least a fraction of the formed carbon monoxide with steam according to the water-gas shift reaction.

$$CH_4 + \tfrac{1}{2}O_2 \rightarrow CO + 2H_2$$

$$CO + H_2O \rightarrow CO_2 + H_2$$

In this way, for example, oxygen can be used to generate more $H_2$.

According to an embodiment, the providing a second feedstock comprises gasification or partial oxidation of biomass. According to an embodiment, the biomass comprises cellulose. According to an embodiment, the biomass comprises lignin. According to an embodiment, biomass is reacted with a controlled amount of oxygen and/or steam into carbon monoxide, hydrogen, and carbon dioxide. According to an embodiment, the method further comprises reacting at least a fraction of the formed carbon monoxide with steam according to the water-gas shift reaction.

$$(C_6H_{10}O_5)n + O_2 + H_2O \rightarrow CO + CO_2 + H_2 \text{ (shown for cellulose, not balanced)}$$

$$CO + H_2O \rightarrow CO_2 + H_2$$

According to an embodiment, the providing a second feedstock comprises coal gasification. According to an embodiment, hydrogen is produced by first reacting coal with oxygen and steam under high pressures and temperatures to form synthesis gas. According to an embodiment, the method further comprises reacting at least a fraction of the formed carbon monoxide with steam according to the water-gas shift reaction.

$$CH_{0.8} + O_2 + H_2O \rightarrow CO + CO_2 + H_2 \text{ (not balanced)}$$

$$CO + H_2O \rightarrow CO_2 + H_2$$

According to an embodiment, the providing a second feedstock comprises at least one of partial oxidation and biomass gasification. According to an embodiment, the providing a second feedstock comprises reaction with oxygen. According to an embodiment, the providing a second feedstock comprises electrolysis, which electrolysis generates oxygen and at least a fraction of the generated oxygen is used for further providing the second feedstock. According to an embodiment, the providing a second feedstock comprises electrolysis and at least one of partial oxidation and biomass gasification, electrolysis generates oxygen and at least a fraction of the generated oxygen is used for at least one of partial oxidation and biomass gasification.

Figure 2:
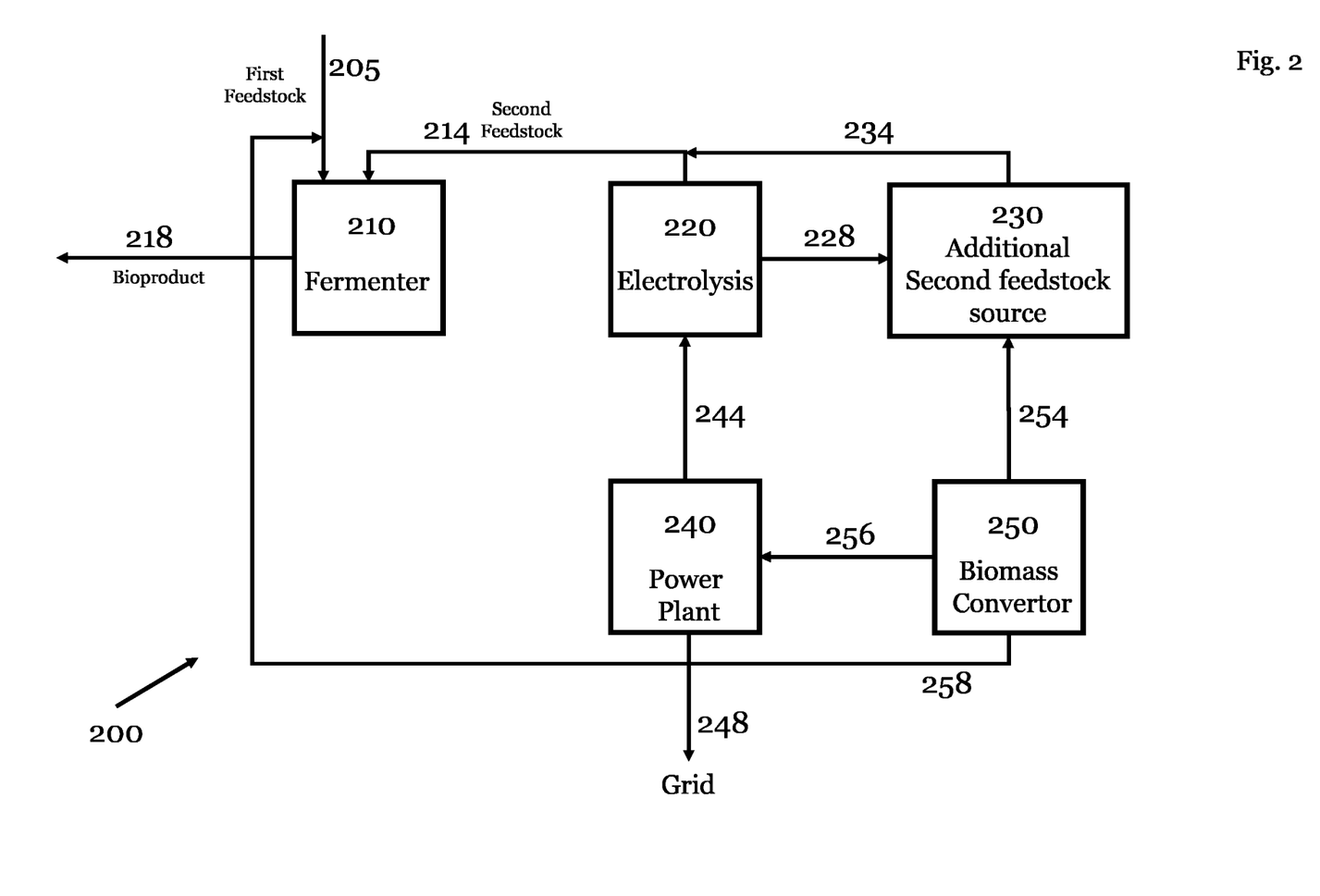
FIG. 2 shows an embodiment example of the integrated mixotrophic fermentation method.

FIG. 2 shows an embodiment example of the integrated mixotrophic fermentation method (200) fermenter (210), containing an isolated naturally acetogenic organism, is provided with a first feedstock (205) comprising a carbon source and a second feedstock (214) comprising $H_2$ resulting from Electrolysis (220) and produce at least one bioproduct (218). The second feedstock (234) alternatively or additionally can be provided by an operation (230) selected from at least one of (a) hydrocarbon reforming, (b) biomass-derived liquid reforming; (c) partial oxidation; (d) biomass gasification, (e) coal gasification, and (f) water-gas shift reaction.

According to the exemplary embodiment, the electrolysis (220), generates in addition to the second feedstock (214) oxygen and at least a fraction of the generated oxygen (228) is used for providing a second feedstock (234) via at least one of partial oxidation and biomass gasification (230).

The method further comprises a biomass convertor (250) processing biomass to produce separated carbohydrate (258) and separated lignin (256), separated carbohydrate is used for providing the first feedstock (205). The method further comprises burning or partially oxidizing at least a fraction of the separated lignin (256) to generate electricity (240) and using at least a fraction of the electricity (244) in the electrolysis (220). According to an embodiment, the generated electricity can be provided to the grid (248). According to an embodiment, the method further comprises gasifying (230) at least a fraction of the separated lignin (254) for providing the second feedstock.

According to an embodiment, the electrolysis is operated at off-peak hours, e.g. during night hours. According to an embodiment, the electrolysis is operated with interruptible power from the grid.

According to an embodiment, the method further comprises processing a lignocellulosic biomass to produce a separated carbohydrate solution and separated lignin and using the separated carbohydrate solution in the providing a first feedstock. As used herein, the term lignocellulosic biomass refers to biomass comprising cellulose and lignin. According to an embodiment, the processed lignocellulosic biomass further comprises hemicellulose. According to an embodiment, the processing a lignocellulosic biomass comprises hydrolysis of hemicellulose, hydrolysis of cellulose or both. According to an embodiment, the hydrolysis comprises at least one of hydro-thermal treatment, acid-catalyzed hydrolysis and enzyme-catalyzed hydrolysis. According to an embodiment, the processing further comprises separating the carbohydrate solution from the lignin to form separated carbohydrate solution and separated lignin.

According to an embodiment the separated carbohydrate solution is used, as such or after modification, to form the fermentation medium first feedstock. According to an embodiment, the method further comprises treating the separated carbohydrate solution for removal of solutes, if such solutes hinder fermentation, e.g. furfural, levulinic acid, formic acid, acetic acid, hydroxymethyl furfural, phenolic molecules like 4-hydroxy-3-methoxyphenyl and 4-hydroxy-3,5-dimethylphenyl moieties. According to an embodiment, the fermentation medium further comprises a nitrogen source.

According to an embodiment, the method comprises processing a lignocellulosic biomass to produce separated carbohydrate solution and separated lignin and burning and/or partially oxidizing at least a fraction of the separated lignin to generate electricity. According to an embodiment, the method further comprises using at least a fraction of the electricity in the electrolysis. According to an embodiment, the method further comprises providing at least a fraction of the generated electricity to the grid at peak hours, e.g. during day time. According to an embodiment, the method further comprises providing at least a fraction of the generated electricity to the grid on demand.

According to an embodiment, the method comprises electrolysis to produce hydrogen, and the electrolysis is conducted at off-peak hours and/or with interruptible power. According to an embodiment, the method further comprises storing of at least a fraction of the produced hydrogen and using at least a fraction of the stored hydrogen to provide the second feedstock, e.g. during peak hours.

According to an embodiment, the method comprises generating electricity, e.g. by burning separated lignin, providing a fraction of the generated electricity to the grid at peak hours and/or on demand. According to an embodiment, the method further comprises using another fraction of the generated electricity in electrolysis to produce hydrogen at off-peak hours.

According to an embodiment, the method comprises processing a lignocellulosic biomass to produce a separated carbohydrate solution and separated lignin and further comprises gasifying at least a fraction of the separated lignin for providing the second feedstock.

According to an embodiment, the first feedstock comprises a carbon source selected from carbohydrates, glycerol, methanol and combinations thereof. According to an embodiment, the carbon source is selected from glucose and sucrose.

According to an embodiment, the carbohydrate comprises monosaccharides, such as glucose, fructose and xylose, disaccharides, such as sucrose, oligosaccharides, such as dextrins, polysaccharides, such as starch, xylan, cellulose and hemicellulose and combinations thereof. According to an embodiment, the carbohydrate comprises hexoses, such as glucose and fructose, pentoses, such as xylose and arabinose and combinations thereof.

According to an embodiment, the organism metabolizes $CO_2$ produced on metabolizing the carbon source.

According to an embodiment, the provided first feedstock, the provided second feedstock or both comprise supplemented $CO_2$. As used herein, the term supplemented $CO_2$ refers to $CO_2$ other than that generated on metabolizing the first feedstock carbon source. According to an embodiment, the supplemented $CO_2$ is generated in another fermentation process, e.g. in a conventional heterotrophic fermentation for ethanol production.

According to an embodiment, the fermentation medium further comprises CO. According to an embodiment, the fermentation medium further comprises a steel mill produced CO composition. According to an embodiment, the fermentation medium may further comprise a steel mill gas composition. For example, the fermentation medium may comprise a steel mill gas composition comprising 40-80% CO, 10-25% $CO_2$, 2-5% $H_2$, and 15-35% $N_2$. In an embodiment, the fermentation medium may comprise a steel mill gas composition comprising 60-70% CO, 15-20% $CO_2$, 3-4% $H_2$, and 20-30% $N_2$. In an embodiment, the fermentation medium may comprise a steel mill gas composition comprising 43-55% CO, 17-20% $CO_2$, 2-3% $H_2$, and 25-34% $N_2$.

According to an embodiment, the organism is acetogenic and the first feedstock comprises at least one non-preferred carbon source, for example, a non-preferred sugar. As used herein, the term non-preferred carbon source refers to a carbon source that is metabolized by the native form of the organism at a rate of less than 0.01 g/hr/g cell mass, less than 0.005 g/hr/g cell mass, or less than 0.002 g/hr/g cell mass. Such a carbon source may be a carbohydrate, a sugar (e.g., glucose) or glycerol. Such a non-preferred carbon source may also be methanol. The non-preferred carbon source may also be an oxygen-containing organic compound. According to an embodiment, the non-preferred carbon source comprises at least 50%, at least 60%, at least 70%, at least 80% or at least 90% of the first feedstock. According to an embodiment, the concentration of the non-preferred carbon source in the provided fermentation medium is in a range between 2 g/L and 50 g/L.

According to an embodiment, the non-preferred sugar is selected from the group consisting of glucose, mannose, galactose, maltose, sucrose, lactose, cellobiose, and mixtures thereof. According to an embodiment, the non-preferred sugar comprises glucose.

According to an embodiment, the first feedstock further comprises at least one preferred sugar. As used herein, the term preferred sugar refers to a sugar that is metabolized by the native form of the organism at a rate greater than 0.01 g/hr/g cell mass.

According to an embodiment, the preferred sugar is selected from the group consisting of fructose, xylose, arabinose, ribose, and mixtures thereof. According to an embodiment, the provided fermentation medium comprises the preferred sugar and the non-preferred sugar concurrently. According to an embodiment, the provided fermentation medium comprises first the preferred sugar and then the non-preferred sugar.

According to an embodiment, the non-preferred sugar is metabolized at a rate greater than 0.01 g/hr/g cell mass. Metabolism rates of a non-preferred sugar of greater than 0.01 g/hr/g cell mass may be achieved by an organism that has been genetically modified for increased non-preferred sugar metabolism. In an embodiment, the non-preferred sugar may be metabolized by a genetically modified organism at a rate greater than 0.02 g/hr/g, greater than 0.04 g/hr/g cell mass, greater than 0.06 g/hr/g, greater than 0.08 g/hr/g cell mass, greater than 0.1 g/hr/g, greater than 0.12 g/hr/g cell mass, greater than 0.14 g/hr/g, greater than 0.16 g/hr/g cell mass, greater than 0.18 g/hr/g, greater than 0.2 g/hr/g cell mass, or greater than 0.26 g/hr/g.

According to an embodiment, metabolizing of the first feedstock does not inhibit the metabolizing of the second feedstock.

According to an embodiment, the first feedstock and the second feedstock are present in the fermentation medium at the same time. According to an embodiment, the fermentation medium comprises concurrently both the first feedstock and the second feedstock during at least a fraction of the culturing time, e.g., during at least 30% of the time, at least 40%, at least 50%, at least 60%, at least 70%, at least 80% or at least 90% of the time.

According to an embodiment, the method further comprises providing a fermentation medium comprising the first feedstock and the second feedstock. According to an embodiment, providing a fermentation medium comprises preparing an aqueous solution comprising the first feedstock and the second feedstock. According to an embodiment, providing comprises supplementing at least one of the first feedstock and the second feedstock during culturing. According to an embodiment, the fermentation medium comprises initially only the first feedstock and then the second feedstock is supplemented. According to an embodiment, supplementing the second feedstock is done before the first feedstock is fully utilized, e.g., at the time the first feedstock is only 10%, 20%, 30% or 40% utilized.

According to an embodiment, the second feedstock comprises a gaseous compound and the gaseous compound is supplemented to the fermentation medium, e.g., via bubbling the gaseous compound through the medium. The methods for supplementing the fermentation medium and/or the feedstock with a carbon source are not limited, and include, for example, exogenously feeding a gaseous compound, such as hydrogen, CO or $CO_2$ or adding a carbon source and/or feedstock and/or additional components to an initially provided fermentation medium or feedstock later in time during fermentation.

According to an embodiment, the fermentation medium is kept during at least a fraction of the culturing time at a super-atmospheric pressure, e.g., during at least 30% of the time, at least 40%, at least 50%, at least 60%, at least 70%, at least 80% or at least 90% of the time. According to an embodiment, the super-atmospheric pressure is in the range between about 1.1 bar and about to bar.

According to an embodiment, the method is characterized by a carbon yield of at least 70%, at least 80%, at least 90%, at least 100%, at least 110%, at least 120%, at least 130%, at least 140%, at least 150%, or at least 160%. As used herein carbon yield is calculated by total amount of carbon in produced bioproducts divided by the total amount of carbon metabolized from the first feedstock. According to an embodiment, the bioproduct comprises ethanol and the method is characterized in carbon yield of at least 67%, at least 69%, at least 71%, at least 73% or at least 75%. According to an embodiment, the bioproduct is ethanol and the method is characterized in carbon yield of at least 67%, at least 69%, at least 71%, at least 73% or at least 75%, wherein carbon yield is calculated by total amount of carbon in produced ethanol divided by the total amount of carbon metabolized from the first feedstock.

According to an embodiment, the method yields a greater amount of the at least one bioproduct than the at least one bioproduct produced by heterotrophic fermentation with the same organism under the same conditions.

According to an embodiment, the method yields a greater amount of the at least one bioproduct than the combined amounts of the at least one bioproduct produced by heterotrophic and autotrophic fermentation with the same organism under the same conditions. The embodiment is exemplified by comparing three cases of fermenting with a given organism capable of and/or configured for use in the method. In the first case (referred to herein as heterotrophic fermentation), a microorganism is cultured in a fermentation medium comprising a first feedstock to form a heterotrophic fermentation broth. In the second case (referred to herein as autotrophic fermentation), the microorganism is cultured in a fermentation medium comprising a second feedstock to form an autotrophic fermentation broth. In the third case (referred to herein as mixotrophic fermentation), a microorganism is cultured in a fermentation medium comprising a mixture of the first feedstock and the second feedstock to form a mixotrophic fermentation broth. At the end of culturing time, the autotrophic fermentation broth is mixed with the heterotrophic fermentation broth to form a mixed fermentation broth. According to the embodiment, the mixotrophic fermentation method may achieve greater production of a target bioproduct or a combination of target bioproducts than the combined amounts produced by heterotrophic and autotrophic fermentation with the same microorganism under the same conditions. The nature of bioproducts in the mixotrophic fermentation and/or the molar ratio between the bioproducts (in case of forming multiple bioproducts), may differ from those of the mixed fermentation broth.

According to an embodiment, the method produces at least one bioproduct and acetic acid as a second bioproduct and the amount of acetic acid produced per biomass unit weight is less than about 50% of that produced in autotrophic fermentation with the same organism under the same conditions.

According to an embodiment, the $^{13}C/^{12}C$ isotope ratio of the carbon present in the bioproduct is less than that of atmospheric $CO_2$. A $^{13}C/^{12}C$ isotope ratio may be used as an indicator of nutrient cycling. For example, according to an embodiment, the bioproduct is characterized by a $^{13}C/^{12}C$ isotope ratio of less than that of atmospheric $CO_2$. In such a case, the $^{13}C/^{12}C$ isotope ratio would be indicative of production of the bioproduct from a non-atmospheric $CO_2$ source, for example, CO, $CO_2$, carbonate, bicarbonate, methanol or mixtures thereof present in the second feedstock.

According to an embodiment, the bioproduct is non-naturally occurring. As used herein a non-naturally occurring bioproduct is a product which is unattainable by the organism when cultured in autotrophic conditions or is produced from a metabolic pathway not native to the organism.

According to an embodiment, the bioproduct is selected from the group consisting of alcohols, organic acids and ketones. According to an embodiment, the bioproduct is selected from the group consisting of even numbered primary alcohols, odd numbered secondary alcohols, organic acids of less than 7 carbons, C3 compounds, C4 compounds, and mixtures thereof.

According to an embodiment, the bioproduct comprises ethanol. According to an embodiment, the bioproduct is ethanol.

According to an embodiment, the bioproduct comprises acetone. According to an embodiment, the bioproduct is acetone.

According to an embodiment, the bioproduct comprises isopropanol. According to an embodiment, the bioproduct is isopropanol.

According to an embodiment, the bioproduct comprises butanol. According to an embodiment, the bioproduct is butanol. According to an embodiment, the butanol is selected from the group consisting of normal butanol, isobutanol, secondary butanol and mixtures thereof.

According to an embodiment, the bioproduct comprises butyric acid. According to an embodiment, the bioproduct is butyric acid.

According to an embodiment, the bioproduct is selected from the group consisting of acetic acid, acetone, propionic acid, butyric acid, hexanoic acid, 3-hydroxypropionic acid, 3-hydroxybutyric acid, crotonic acid, acetoacetic acid, lactic acid, 2-hydroxyisobutyric acid, 3-methylbutanoic acid, ethanol, butanol, crotyl alcohol, hexanol, acetone, isopropanol, 2,3-butanediol, acetoin, 1,3-propanediol, and combinations thereof.

According to an embodiment, the broth comprises a first bioproduct and a second bioproduct, wherein the first bioproduct is selected from the group consisting of acetoacetic acid, acetone, isopropanol, 3-hydroxybutyric acid, 2-hydroxyisobutyric acid, and combinations thereof, the second bioproduct is selected from the group consisting of ethanol, butanol, crotyl alcohol, hexanol, and combinations thereof, and the molar ratio between the first bioproduct and the second bioproduct is in the range from 0.1 to 0.95.

Optionally the method further comprises separating the bioproduct from the broth. Any separation method is suitable. According to various embodiments, separating comprises distillation, solvent extraction, crystallization, ion-exchange, membrane separation and combinations thereof. In an embodiment, the bioproduct may be separated by evaporation, wherein evaporation means any transfer into the vapor phase, e.g., distillation, stripping, etc. In another embodiment, the bioproduct may be, for example, acetone, and the method includes catalytically converting the separated acetone into at least one acetone derivative. In an embodiment, such a method may comprise catalytically converting the separated acetone into one or more of mesitylene (1-3-5-trimethylbenzene), isophthalic acid, uvitic acid, and meta-xylene.

The subject matter disclosed herein provides advantages and combinations of features not previously achieved or even appreciated by prior fermentation or electricity-producing methods. For example, the subject matter disclosed herein integrates production of hydrogen via conventional electrolysis methods with mixotrophic fermentation processes that utilize such hydrogen in a feedstock for higher yields of bioproducts. Further to this, byproducts of the mixotrophic fermentation process may themselves be utilized as an energy source, i.e., a lignocellulosic biomass may, for example, be used to produce a carbohydrate solution and lignin—the carbohydrate solution may be utilized as part of a first feedstock and the lignin produced during mixotrophic fermentation may be burned to generate power, which power can be transferred to a conventional power grid to provide energy/electricity for consumption by consumers or to generate more hydrogen.

Moreover, the hydrogen produced and the lignin that are produced may serve as energy stores for later use, such that the methods achieve additional utility. There is a huge difference between electricity demand during peak vs. off-peak hours. Utilizing methods as disclosed herein it is possible to burn lignin at desired times, e.g., during peak hours. Electricity from the grid may also be conveniently used during off-peak hours to produce hydrogen to be utilized immediately or stored for later use in mixotrophic methods as disclosed herein. Indeed, energy may be stored in the form of hydrogen or unused lignin. Lignin can be partially oxidized to generate hydrogen.

The methods disclosed herein are not limiting and are integrative. As described above, methods as disclosed herein include features such as hydrogen production (e.g., from water at relatively high quality (with or without addition of acid) via conventional electrolysis methods), utilization of lignocellulosic material for bioproduct formation, and electricity or other energy production from the lignin produced via the disclosed fermentation methods.

EXAMPLES

Example 1

Two acetogenic clostridial strains were tested for mixotrophic growth: *Clostridium ljungdahlii* DSM 13528 and *Clostridium autoethanogenum* DSM 10061. Both strains were cultured under three conditions: 10 g/l of fructose (first feedstock) with a $N_2$ headspace at 20 psig (referred to as heterotrophic fermentation), no fructose with a syngas headspace ($CO:CO_2:H_2:N_2$, 55:10:20:15, second feedstock) headspace at 30 psig (autotrophic fermentation), and 10 g/l of fructose with a syngas headspace ($CO:CO_2:H_2:N_2$, 55:10:20:15, second feedstock) headspace at 30 psig (mixotrophic fermentation). In addition, a control culture of *C. acetobutylicum* ATCC 824, that cannot metabolize $CO_2$, was prepared using the heterotrophic conditions to compare against the two acetogens. Three biological replicates of each strain were prepared, grown at 37° C. in standard PETC medium and shaken at 200 rpm. The pH was actively controlled with 6M NaOH to keep the pH between 5 and 6. Headspace volumes for the autotrophic and mixotrophic fermentations was replenished every 2-3 days.

Metabolite profiles and carbon yields, also referred to here as carbon efficiencies, are shown in the Tables below. Carbon efficiency is calculated by dividing the total amount of carbon in produced metabolites by the total amount of carbon consumed in the form of sugar. In the case for metabolites derived from acetyl-CoA, the theoretical maximum without $CO_2$ fixation is 67%.

TABLE 1

Heterotrophic fermentation of *C. ljungdahlii*.
Heterotrophic culture (10 g/l fructose with $N_2$ headspace)

| | Concentration (mM) | | | | | |
|---|---|---|---|---|---|---|
| Hour | Fructose | Acetate | Ethanol | 2,3-Butanediol | Lactate | Carbon efficiency |
| 0 | 55.78 | 0.00 | 0.00 | 0.00 | 0.14 | — |
| 29 | 50.08 | 10.69 | 3.87 | 0.00 | 0.12 | 86% |
| 47 | 40.57 | 34.45 | 5.82 | 0.00 | 0.07 | 88% |
| 70 | 27.47 | 68.20 | 4.78 | 0.00 | 0.12 | 86% |
| 97 | 13.98 | 98.18 | 5.09 | 0.10 | 0.16 | 83% |
| 121 | 4.80 | 120.33 | 6.21 | 0.17 | 0.23 | 83% |
| 144 | 0.25 | 129.28 | 7.51 | 0.19 | 0.33 | 83% |

TABLE 2

Mixotrophic fermentation of *C. ljungdahlii*.
Mixotrophic culture (10 g/l fructose with syngas headspace)

| | Concentration (mM) | | | | | |
|---|---|---|---|---|---|---|
| Hour | Fructose | Acetate | Ethanol | 2,3-Butanediol | Lactate | Carbon efficiency |
| 0 | 57.41 | 0.00 | 0.00 | 0.00 | 0.16 | — |
| 19 | 57.19 | 1.01 | 0.14 | 0.00 | 0.21 | 220% |
| 42 | 49.60 | 20.52 | 1.87 | 0.03 | 0.20 | 97% |
| 67 | 37.20 | 86.87 | 4.93 | 0.92 | 0.14 | 155% |
| 93 | 34.56 | 112.37 | 5.56 | 3.55 | 0.72 | 184% |
| 114 | 33.32 | 120.78 | 7.15 | 5.48 | 1.57 | 195% |
| 138 | 31.38 | 127.57 | 7.90 | 6.64 | 1.89 | 194% |
| 162 | 29.34 | 134.32 | 8.78 | 7.39 | 2.29 | 192% |

TABLE 3

Autotrophic fermentation of *C. ljungdahlii*.
Autotrophic culture (syngas headspace)

| | Concentration (mM) | | | | | |
|---|---|---|---|---|---|---|
| Hour | Fructose | Acetate | Ethanol | 2,3-Butanediol | Lactate | Carbon efficiency* |
| 0 | 0.00 | 0.00 | 0.00 | 0.00 | 0.16 | — |
| 25 | 0.00 | 0.43 | 0.00 | 0.00 | 0.16 | — |
| 41 | 0.00 | 1.18 | 0.10 | 0.00 | 0.17 | — |
| 65 | 0.00 | 8.15 | 0.98 | 0.18 | 0.32 | — |
| 90 | 0.00 | 38.05 | 4.17 | 1.86 | 0.51 | — |
| 113 | 0.00 | 39.85 | 3.43 | 1.85 | 0.36 | — |
| 138 | 0.00 | 39.25 | 7.27 | 1.98 | 0.29 | — |
| 164 | 0.00 | 31.32 | 23.67 | 3.18 | 0.35 | — |
| 185 | 0.00 | 58.88 | 20.79 | 3.93 | 0.17 | — |
| 209 | 0.00 | 68.27 | 18.09 | 4.03 | 0.11 | — |
| 233 | 0.00 | 57.82 | 33.30 | 4.90 | 0.36 | — |

*Carbon efficiency cannot be determined for autotrophic fermentations because there is no sugar substrate.

TABLE 4

Heterotrophic fermentation of *C. autoethanogenum*.
Heterotrophic culture (10 g/l fructose with $N_2$ headspace)

| | Concentration (mM) | | | | |
| --- | --- | --- | --- | --- | --- |
| Hour | Fructose | Acetate | Ethanol | 2,3-Butanediol | Lactate | Carbon efficiency |

| Hour | Fructose | Acetate | Ethanol | 2,3-Butanediol | Lactate | Carbon efficiency |
| --- | --- | --- | --- | --- | --- | --- |
| 0 | 54.93 | 0.00 | 0.00 | 0.00 | 0.14 | — |
| 23 | 54.04 | 4.50 | 0.52 | 0.00 | 0.14 | 195% |
| 50 | 44.38 | 15.91 | 8.52 | 0.03 | 0.14 | 78% |
| 74 | 23.82 | 37.47 | 23.84 | 1.10 | 0.42 | 69% |
| 97 | 0.50 | 71.35 | 34.07 | 2.57 | 1.18 | 69% |
| 123 | 0.12 | 77.12 | 32.10 | 2.75 | 1.20 | 71% |

TABLE 5

Mixotrophic fermentation of *C. autoethanogenum*.
Mixotrophic culture (10 g/l fructose with syngas headspace)

| Hour | Fructose | Acetate | Ethanol | 2,3-Butanediol | Lactate | Carbon efficiency |
| --- | --- | --- | --- | --- | --- | --- |
| 0 | 58.11 | 0.00 | 0.00 | 0.00 | 0.16 | — |
| 19 | 58.27 | 0.20 | 0.00 | 0.00 | 0.16 | — |
| 42 | 52.92 | 8.23 | 3.60 | 0.00 | 0.21 | 78% |
| 67 | 35.95 | 69.41 | 17.77 | 0.63 | 0.25 | 134% |
| 93 | 26.40 | 92.50 | 31.13 | 3.10 | 0.76 | 138% |
| 114 | 14.39 | 121.79 | 44.71 | 8.18 | 2.44 | 142% |
| 138 | 6.71 | 164.11 | 50.85 | 13.05 | 3.86 | 160% |
| 162 | 1.16 | 168.14 | 67.42 | 17.04 | 4.98 | 162% |

TABLE 6

Autotrophic fermentation of *C. autoethanogenum*.
Autotrophic culture (syngas headspace)

| Hour | Fructose | Acetate | Ethanol | 2,3-Butanediol | Lactate | Carbon efficiency* |
| --- | --- | --- | --- | --- | --- | --- |
| 0 | 0.00 | 0.00 | 0.00 | 0.00 | 0.16 | — |
| 25 | 0.00 | 1.84 | 0.00 | 0.00 | 0.13 | — |
| 41 | 0.00 | 8.24 | 1.48 | 0.00 | 0.13 | — |
| 65 | 0.00 | 41.96 | 6.72 | 0.21 | 0.04 | — |
| 90 | 0.00 | 38.55 | 10.56 | 0.30 | 0.13 | — |
| 113 | 0.00 | 39.52 | 12.44 | 0.31 | 0.13 | — |
| 138 | 0.00 | 37.94 | 19.51 | 0.69 | 0.20 | — |
| 164 | 0.00 | 25.02 | 39.80 | 3.27 | 0.55 | — |
| 185 | 0.00 | 69.78 | 26.19 | 5.00 | 0.13 | — |
| 209 | 0.00 | 72.45 | 25.86 | 5.12 | 0.12 | — |
| 233 | 0.00 | 67.61 | 32.90 | 5.29 | 0.19 | — |

*Carbon efficiency cannot be determined for autotrophic fermentations because there is no sugar substrate.

TABLE 7

Heterotrophic fermentation of *C. acetobutylicum*.
Heterotrophic culture (10 g/l fructose with $N_2$ headspace)

| Hour | Glucose/Fructose | Acetate | Butyrate | Ethanol | Butanol | Lactate | Acetoin | Carbon efficiency |
| --- | --- | --- | --- | --- | --- | --- | --- | --- |
| 0 | 90.97 | 3.31 | 0.65 | 0.00 | 0.00 | 0.4 | 0.00 | — |
| 12 | 67.88 | 10.99 | 13.06 | 2.21 | 0.36 | 4.20 | 2.19 | 66% |
| 24 | 47.06 | 16.84 | 24.02 | 2.55 | 1.73 | 10.10 | 1.95 | 64% |
| 48 | 47.13 | 17.00 | 23.74 | 2.34 | 2.09 | 10.09 | 2.46 | 65% |

The results for the two acetogens exemplify the non-additive, i.e., synergistic nature of the mixotrophic fermentation. Combining the heterotrophic fermentation broth with the autotrophic fermentation broth, the mixotrophic fermentation broth is not achieved. For example, adding the endpoints of heterotrophic and autotrophic for *C. ljungdahlii*, the molar ratios of acetate, ethanol, 2,3-butanediol, and lactate are: 0.80, 0.18, 0.02, and 0.003, respectively. In comparison, the ratios for mixotrophic fermentation are 0.88, 0.06, 0.05, and 0.01, respectively. The fraction of both 2,3-butanediol and lactate increase, while the fraction of ethanol decreases. The same is true for *C. autoethanogenum*.

Additionally, the carbon efficiencies under mixotrophic fermentation demonstrate that both sugar and gases are being metabolized, since the efficiencies are >100%. Even under heterotrophic conditions for the two acetogens, the carbon efficiencies are greater than the theoretically possible 67%, demonstrating that some of the evolved $CO_2$ from glycolysis is being metabolized into bioproducts. In comparison, the carbon efficiencies for *C. acetobutylicum* are only ~65%, which is the maximum without being able to metabolize $CO_2$.

Example 2

*C. ljungdahlii* DSM 13528 has a native secondary alcohol dehydrogenase gene (accession number CLJU_c24860) with a nucleic acid sequence of:

(SEQ ID NO: 1)
ATGAAAGGTTTTGCAATGTTAGGTATTAACAAATTAGGATGGATTGA

AAAGAAAAACCCAGTGCCAGGTCCTTATGATGCGATTGTACATCCTCTAG

CTGTATCCCCATGTACATCAGATATACATACGGTTTTTGAAGGAGCACTT

GGTAATAGGGAAAATATGATTTTAGGCCATGAAGCTGTAGGTGAAATAGC

CGAAGTTGGCAGCGAAGTTAAAGATTTTAAAGTTGGCGATAGAGTTATCG

TACCATGCACAACACCTGACTGGAGATCTTTAGAAGTCCAAGCTGGTTTT

CAGCAGCATTCAAACGGTATGCTTGCAGGATGGAAGTTTTCCAATTTTAA

AGATGGTGTATTTGCAGATTACTTTCATGTAAACGATGCAGATATGAATC

TTGCCATACTCCCAGATGAAATACCTTTAGAAAGTGCAGTTATGATGACA

GACATGATGACTACTGGTTTTCATGGAGCAGAACTTGCAGACATAAAAAT

GGGCTCCAGCGTTGTAGTAATTGGTATAGGAGCTGTTGGATTAATGGGAA

TAGCCGGTTCCAAACTTCGAGGAGCAGGCAGAATTATCGGTGTTGGAAGC

AGACCTGTTTGTGTTGAAACAGCTAAATTTTATGGAGCAACTGATATTGT

```
-continued
AAATTATAAAAATGGTGATATAGTTGAACAAATCATGGACTTAACTCATG

GTAAAGGTGTAGACCGTGTAATCATGGCAGGCGGTGGTGCTGAAACACTA

GCACAAGCAGTAACTATGGTTAAACCTGGCGGCGTAATTTCTAACATCAA

CTACCATGGAAGCGGTGATACTTTACCAATACCTCGTGTTCAATGGGGCT

GCGGCATGGCTCACAAAACTATAAGAGGAGGATTATGCCCCGGCGGACGT

CTTAGAATGGAAATGCTAAGAGATCTTGTTCTATATAAACGTGTTGATTT

GAGTAAACTTGTTACTCATGTATTTGATGGTGCAGAAAATATTGAAAAGG

CCCTTTTGCTTATGAAAAATAAGCCAAAAGATTTAATTAAATCAGTAGTT

ACATTCTAA.
```

This gene was deleted from the chromosome and replaced with a chloramphenicol acetyltransferase (CAT) gene, which confers resistance to the antibiotic chloramphenicol or thiamphenicol. This new strain is termed Clj ΔSADH.

A plasmid expressing the genes for thiolase (also known as acetyl-CoA acetyltransferase), acetoacetate transferase subunit A, acetoacetate transferase subunit B, and acetoacetate decarboxylase was transformed into this deletion strain. All genes came from *C. acetobutylicum* ATCC 824.

The deletion strain with the plasmid was grown anaerobically in media containing 5 g/l of fructose. The headspace consisted of $N_2$, $CO_2$, and $H_2$ (85%, 10%, 5%, respectively) at 1 atm.

This strain produced primarily acetone (a non-native metabolite) and acetate (a native metabolite). Table 8 shows the metabolite production of this strain.

TABLE 8

| Acetone titer (g/L) | Acetate titer (g/L) | Acetate in metabolite pool (wt %) | Sugar consumed (g/L) | Acetone mass yield (wt %) | Acetone yield if all acetate were re-assimilated (wt %) |
|---|---|---|---|---|---|
| 2.65 | 0.77 | 22.0% | 6.79 | 39.1% | 45.6% |

Mass yield is calculated by dividing total concentration of products produced by the total amount of sugar consumed. The mass yield for this strain is 39.1% for acetone, which is greater than can be achieved on sugar alone (a theoretical maximum of 32 wt %). This demonstrates the ability of this strain to produce enhanced mass yields of a non-native metabolite.

The invention claimed is:

1. An integrated mixotrophic fermentation method comprising
   (i) providing an isolated naturally acetogenic bacterium belonging to the Clostridia family;
   (ii) providing a first feedstock comprising a non-preferred carbon source for use in a fermentation medium, wherein said non-preferred carbon source is selected from the group consisting of a carbohydrate, a sugar and glycerol;
   (iii) providing a second feedstock comprising elemental hydrogen gas for use in said fermentation medium; wherein said providing a second feedstock comprises performing electrolysis; and
   (iv) culturing said bacterium in said fermentation medium, whereby both feedstocks are metabolized and a fermentation broth is formed, which broth comprises at least one bioproduct.

2. The method of claim 1, wherein said bacterium is not naturally occurring.

3. The method of claim 1, wherein said providing a second feedstock further comprises at least one operation selected from the group consisting of (a) hydrocarbon reforming, (b) biomass-derived liquid reforming; (c) partial oxidation; (d) biomass gasification, (e) coal gasification, and (f) water-gas shift reaction.

4. The method of claim 1, wherein said providing a second feedstock further comprises at least one of partial oxidation and biomass gasification.

5. The method of claim 1, wherein said electrolysis generates oxygen and wherein at least a fraction of said generated oxygen is used for providing said second feedstock via at least one of partial oxidation and biomass gasification.

6. The method of claim 1, further comprising (a) processing a lignocellulosic biomass to produce a separated carbohydrate solution and separated lignin and (b) using said separated carbohydrate solution in said providing a first feedstock.

7. The method of claim 6, further comprising burning or partially oxidizing at least a fraction of said separated lignin to generate electricity and using at least a fraction of said electricity in said electrolysis.

8. The method of claim 6, further comprising gasifying at least a fraction of said separated lignin for providing said second feedstock.

9. The method of claim 1, wherein said provided first feedstock, said provided second feedstock or both comprise supplemented $CO_2$.

10. The method of claim 1, wherein the carbon yield based on the total amount of carbon in produced bioproducts divided by the total amount of carbon metabolized from said carbon source is at least 67%.

11. The method of claim 1, wherein said bioproduct comprises ethanol and wherein the carbon yield based on the total amount of carbon in produced ethanol divided by the total amount of carbon metabolized from said carbon source, is at least 67%.

12. The method of claim 1, wherein the first feedstock comprises a carbohydrate selected from glucose and sucrose, wherein $CO_2$ is produced on metabolizing the carbohydrate and wherein the isolated naturally acetogenic bacterium metabolizes said $CO_2$.

13. The method of claim 1, wherein the first feedstock comprises glycerol, wherein $CO_2$ is produced on metabolizing said glycerol and wherein the isolated naturally acetogenic bacterium metabolizes said $CO_2$.

14. The method of claim 1, wherein said carbon source is metabolized by the native form of the isolated naturally acetogenic bacterium at a rate of less than 0.01 g/hr/g cell mass.

15. The method of claim 1, which yields a greater amount of the at least one bioproduct than the combined amounts of the at least one bioproduct produced by heterotrophic and autotrophic fermentation with the same organism under the same conditions.

16. The method of claim 1, which yields a greater amount of the at least one bioproduct than the amount of the at least one bioproduct produced by heterotrophic fermentation with the same organism under the same conditions.

17. The method of claim 1, comprising production of a first bioproduct and acetic acid as a second bioproduct, wherein the amount of acetic acid produced per biomass unit weight is less than about 50% of that produced in autotrophic fermentation with the same organism under the same conditions.

18. The method of claim 1, wherein the $^{13}C/^{12}C$ isotope ratio of the carbon present in the bioproduct is less than that of atmospheric $CO_2$.

19. The method of claim 1, wherein said bacterium is selected from *Clostridium ljungdahlii, Clostridium autoethanogenum, Clostridium* ragsdalei, *Clostridium aceticum, Clostridium carboxidivorans, Clostridium drakei, Clostridium formicoaceticum, Clostridium scatologenes, Clostridium glycolicum, Clostridium magnum, Clostridium mayombei,* and *Clostridium methoxybenzovorans.*

20. The method of claim 1, wherein said bioproduct is selected from the group consisting of even numbered primary alcohols, odd numbered secondary alcohols, organic acids of less than 7 carbons, $C_3$ compounds, $C_4$ compounds, and mixtures thereof.

* * * * *